United States Patent
Choung et al.

(10) Patent No.: US 12,011,431 B2
(45) Date of Patent: Jun. 18, 2024

(54) PHARMACEUTICAL COMPOSITION FOR PREVENTING OR TREATING SENSORINEURAL HEARING LOSS, CONTAINING FORSKOLIN AND RETINOIC ACID AS ACTIVE INGREDIENTS

(71) Applicant: AJOU UNIVERSITY INDUSTRY-ACADEMIC COOPERATION FOUNDATION, Gyeonggi-do (KR)

(72) Inventors: Yun-Hoon Choung, Seoul (KR); Yeon Ju Kim, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 729 days.

(21) Appl. No.: 17/265,436

(22) PCT Filed: Aug. 6, 2019

(86) PCT No.: PCT/KR2019/009759
§ 371 (c)(1),
(2) Date: Feb. 2, 2021

(87) PCT Pub. No.: WO2020/032516
PCT Pub. Date: Feb. 13, 2020

(65) Prior Publication Data
US 2021/0299084 A1     Sep. 30, 2021

(30) Foreign Application Priority Data
Aug. 10, 2018 (KR) .................. 10-2018-0093767

(51) Int. Cl.
*A61K 31/352* (2006.01)
*A61K 31/202* (2006.01)
*A61K 45/06* (2006.01)
*A61P 27/16* (2006.01)

(52) U.S. Cl.
CPC .......... *A61K 31/352* (2013.01); *A61K 31/202* (2013.01); *A61K 45/06* (2013.01); *A61P 27/16* (2018.01)

(58) Field of Classification Search
CPC ...... A61K 31/352; A61K 31/202; A61P 27/16
See application file for complete search history.

(56) References Cited

U.S. PATENT DOCUMENTS

| 6,268,351 B1 | 7/2001 | Oberholtzer et al. |
| 9,125,894 B2 | 9/2015 | Edge |
| 2002/0176859 A1 | 11/2002 | Gao |

OTHER PUBLICATIONS

Xiangrui Guo et at., "Forskolin protects against cisplatin-induced ototoxicity by inhibiting apoptosis and ROS production", Biomedicine and Pharmacotherapy, 99, 530-536, 2018, 7 pages.
Philippe P. Lefebvre et al., "Retinoic Acid Stimulates Regeneration of Mammalian Auditory Hair Cells", Science. 1993, vol. 260, pp. 692-695, 4 pages.
Moo Jin Baek et al., "Sensorineural Hearing Loss: Causes and Hearing Rehabilitation", Hanyang Medical Reviews, 5:57-65, 2015, 9 pages.
Se-Jin Kim et al., "Bucillamine prevents cisplatin-induced ototoxicity through induction of glutathione and antioxidant genes", Experimental & Molecular Medicine 20(47):e142, 2015, 16 pages.
Müzeyyen Yildirim et al., "Preventing cisplatin induced ototoxicity by N-acetylcysteine and salicylate", Kulak Burun Bogaz Ihtis Derg, 20(4):173-83, 2010, 11 pages.
Kazuto Mishima et al., "Protective effect of cyclic AMP against cisplatin-induced nephrotoxicity", Department of Pharmacy, Kyushu University Hospital, Free Radical Biology Medicine 40(9):1564-77, 2006, 14 pages.
Aditi Gupta et al., "Communication of cAMP by connexin43 gap junctions regulates osteoblast signaling and gene expression", Department of Orthopaedics, University of Maryland School of Medicine, Cellular Signalling 28(8):1048-57, 2016, 10 pages.
Korean Intellectual Property Office, Office Action for KR 10-2018-0093767 dated Oct. 29, 2019.
International Searching Authority, International search report for PCT/KR2019/009759 dated Nov. 11, 2019.

*Primary Examiner* — Kamal A Saeed
(74) *Attorney, Agent, or Firm* — Sughrue Mion, PLLC

(57) ABSTRACT

A pharmaceutical composition containing forskolin and retinoic acid as active ingredients which is suitable for preventing or treating sensorineural hearing loss is disclosed. A pharmaceutical composition containing forskolin and retinoic acid as active ingredients has an excellent effect of preventing, alleviating or treating hearing loss caused by ototoxic drugs during anticancer treatment, and thus is useful as a pharmaceutical composite preparation capable of reducing side effects of anticancer drugs and, additionally, as an agent for preventing or treating sensorineural hearing loss.

11 Claims, 13 Drawing Sheets
(10 of 13 Drawing Sheet(s) Filed in Color)

PHARMACEUTICAL COMPOSITION FOR PREVENTING OR TREATING SENSORINEURAL HEARING LOSS, CONTAINING FORSKOLIN AND RETINOIC ACID AS ACTIVE INGREDIENTS

CROSS-REFERENCE TO RELATED APPLICATIONS

This application is a National Stage of International Application No. PCT/KR2019/009759 filed Aug. 6, 2019, which claims priority under U.S.C. § 119(a) to Korea Patent Application No. 10-2018-0093767 filed on Aug. 10, 2018.

TECHNICAL FIELD

The present invention relates to a composition for preventing or treating sensorineural hearing loss comprising forskolin and retinoic acid as active ingredients, and more particularly to a composition for preventing, alleviating or treating sensorineural hearing loss caused by ototoxic drugs during anticancer therapy.

BACKGROUND ART

Deafness, that is, "hearing loss", refers to a phenomenon in which it becomes difficult to hear sound due to abnormalities in the outer ear, middle ear, or inner ear. Hearing loss is a very common disease occurring in about 15 to 20% of the total population. The percentage of the population suffering from hearing loss is gradually increasing due to environmental pollution and aging in modern society, and it is considerably important to prevent auditory disorders prior to the occurrence thereof because such disorders are permanent. Hearing loss is mainly caused by environmental factors and genetic factors such as suddenness, medications (antibiotics such as aminoglycoside or anticancer drugs), noise, trauma, senility and congenital factors, and is mostly characterized by damage and death of hair cells in the organ of Corti of the inner ear.

For the treatment of sensorineural hearing loss, signaling pathway mechanisms involved in the regeneration of inner ear hair cells and the proliferation and differentiation of hair cells have been actively identified, and in recent years, research on regeneration of hair cells has rapidly progressed through the development of technologies associated with gene therapy (gene editing) or cell transplantation. However, the development of mechanisms, or preventive or therapeutic agents associated with the inhibition and prevention of hearing loss remains unsatisfactory (Baek M. J. et al., Hanyang Med. Rev. 5:57-65, 2015).

Ototoxic hearing loss is an impairment in hearing or equilibrium function caused by the action of drugs used in clinical practice. Current typical ototoxic substances include aminoglycoside-based antibiotics, cisplatin anticancer drugs, diuretics and the like. The ototoxicity of the cisplatin anticancer drug was reported to cause decreased hearing function in about 30% of users and in 50% of children, with a higher incidence of hearing impairment (BRIELLE URCIUOLI, 2018). Nevertheless, cisplatin anticancer drugs are inevitably used in clinical practice due to the excellent anticancer treatment effect thereof. Unlike antibiotic ototoxicity, which mainly damages the hair cells in the inner ear, cisplatin seriously damages not only hair cells, but also supporting cells and spiral ganglion cells.

Attempts to prevent and treat cisplatin anticancer drug-induced hearing loss have mainly focused on the use of antioxidants. In particular, the use of bucillamine, vitamin E, caffeic acid, N-acetylcysteine and the like have been tried (Kim S. J. et al., Exp. Mol. Med. 20(47):e142, 2015; Yildirim M et al., Kulak Burun Bogaz Ihtis Derg. 20(4):173-83, 2010). These antioxidants have shown the effect of reducing ototoxicity by increasing glutathione, inducing antioxidant genes and reducing reactive oxide species (ROS) overactivity, but potent preventive drugs have not been developed yet. Despite many studies attempting to prevent and treat hearing loss, neither a clear molecular mechanism of hearing loss nor an effective method for preventing and treating the same have been proposed to date.

Meanwhile, forskolin is a component contained in the roots of the tropical plant, Coleus forskohlii, and is a low-molecular-weight compound that activates adenylate cyclase and increases cAMP in cells. It has been used for menstrual irregularities for a long time, and is currently known as a potent body fat-burning substance and widely known as a body weight control component. It has been reported that, when cAMP activity is induced with regard to renal toxicity, which is a side effect of cisplatin anticancer drugs, cisplatin-induced oxidative damage in kidney cells is reduced through a pathway for inhibiting the synthesis of reactive oxygen species (ROS) and TNF-alpha (Mishima K et al., Free Radic. Biol. Med. 40(9):1564-77, 2006).

Retinoic acid is an oxidized metabolite that is produced when vitamin A (retinol) is decomposed in vivo, and is an essential component which is involved in the growth and differentiation of epithelial tissues through the regulation of expression of various genes, and plays a major role in the central nervous system, hematopoietic function, and cell survival/death. As retinoic acid has been demonstrated to regulate the differentiation and growth of cancer cells, its therapeutic efficacy has been proven in various cancers such as breast cancer, lung cancer, and head and neck cancer. In addition, it has been reported that the role of retinoic acid in the inner ear is mainly involved in the survival and development of inner ear sensory cells. It was reported that the administration of retinoic acid causes an effect of protecting hearing loss in mice having noise-induced hearing loss, and retinoic-acid-related signals are essential elements of inner ear development since they are involved in the regeneration and differentiation of auditory supporting cells through p27kip and sox2 inhibition.

Therefore, as a result of extensive efforts to identify the molecular mechanism of hearing loss caused by ototoxic drugs during anticancer therapy and to prevent and treat hearing loss, the present inventors have confirmed that administration of a combination of forskolin and retinoic acid is more effective in ameliorating hearing loss and suppressing deterioration in hearing loss compared to administration of either forskolin or retinoic acid alone. Based on this finding, the present invention has been completed.

SUMMARY OF THE INVENTION

It is one object of the present invention to provide a pharmaceutical composition comprising forskolin and retinoic acid as active ingredients for preventing or treating sensorineural hearing loss, which is a side effect of anticancer therapy.

It is another object of the present invention to provide an anticancer adjuvant comprising forskolin and retinoic acid as active ingredients for ameliorating sensorineural hearing loss, and a complex preparation for anticancer treatment comprising the anticancer adjuvant and an anticancer drug as active ingredients.

To achieve the above object, the present invention provides a pharmaceutical composition for preventing or treating sensorineural hearing loss comprising forskolin and retinoic acid as active ingredients.

The present invention also provides an anticancer adjuvant comprising forskolin and retinoic acid as active ingredients for ameliorating sensorineural hearing loss.

The present invention also provides a complex preparation for anticancer treatment comprising the anticancer adjuvant and an anticancer drug as active ingredients.

The present invention also provides a method of preventing or treating sensorineural hearing loss comprising administering forskolin and retinoic acid.

The present invention also provides a use of forskolin and retinoic acid for the prevention or treatment of sensorineural hearing loss.

The present invention also provides a use of forskolin and retinoic acid for the preparation of a medicament for preventing or treating sensorineural hearing loss.

The present invention also provides a method of ameliorating sensorineural hearing loss comprising administering the anticancer adjuvant comprising forskolin and retinoic acid as active ingredients.

The present invention also provides a method of ameliorating sensorineural hearing loss comprising administering the complex preparation for anticancer treatment comprising forskolin and retinoic acid as active ingredients.

The present invention also provides a use of the anticancer adjuvant comprising forskolin and retinoic acid as active ingredients for the amelioration of sensorineural hearing loss.

The present invention also provides a use of the complex preparation for anticancer treatment comprising forskolin and retinoic acid as active ingredients for the amelioration of sensorineural hearing loss.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION AND PREFERRED EMBODIMENTS OF THE INVENTION

Figure 1:
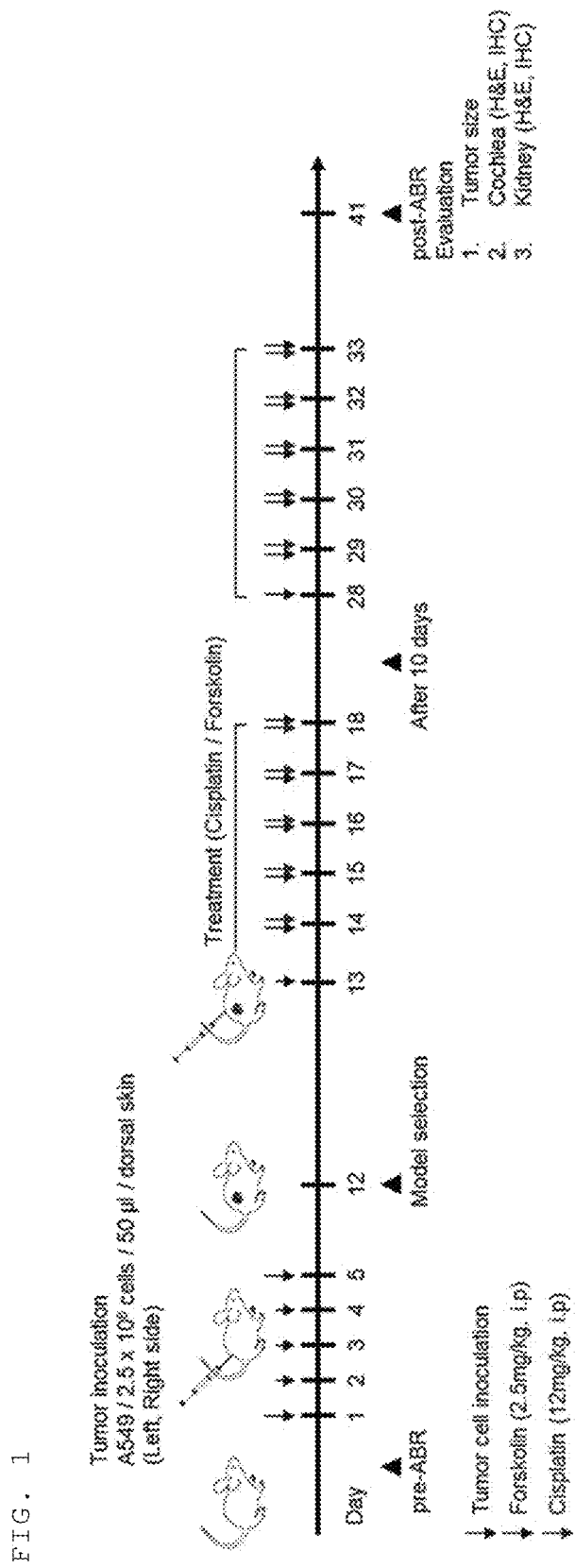
FIG. 1 is a schematic diagram showing construction of a tumor-induced model and an in-vivo experiment using Balb/c/nu/nu mice.

Unless defined otherwise, all technical and scientific terms used herein have the same meanings as appreciated by those skilled in the field to which the present invention pertains. In general, the nomenclature used herein is well-known in the art and is ordinarily used.

In the present invention, it was found that forskolin inhibits and ameliorates hearing loss in an ototoxic hearing loss mouse model, and preserves loss of auditory hair cells, supporting cells, and spiral ganglion cells. In addition, it was found that forskolin did not affect the anticancer effect of cisplatin, which is an anticancer drug that causes ototoxicity. Moreover, it was found that the effect of inhibiting apoptosis of the auditory cell line was remarkably improved by treating the auditory cell line with a combination of forskolin and retinoic acid. That is, it was found that forskolin exerts a synergistic effect on the treatment of hearing loss when administered in combination with retinoic acid.

Accordingly, in one aspect, the present invention is directed to a pharmaceutical composition for preventing or treating sensorineural hearing loss comprising forskolin and retinoic acid as active ingredients.

In the present invention, the sensorineural hearing loss is ototoxic hearing loss caused by ototoxic drugs.

As used herein, the term "sensorineural hearing loss" refers to hearing loss that occurs when the components of the inner ear or accompanying nerve components are affected, and the nerve or sensory component may be contained when the auditory cells or auditory nerve pathways of the brain are affected. Sensory hearing loss may be caused by genetic factors, acoustic trauma (for example, a very loud noise such as an explosion sound), viral infections, drugs or Meniere's disease. Neural hearing loss may be caused by brain tumors, infections or various brain and neurological disorders such as strokes. Some genetic diseases such as Refsum disease (defective accumulation of branched fatty acids) can also cause neurological diseases that affect hearing loss. Auditory nerve pathways are damaged by demyelinating diseases such as idiopathic inflammatory demyelinating diseases (including multiple sclerosis), transverse myelitis, Devic's disease, progressive multifocal leukoencephalopathy, Guillain-Barré syndrome, chronic inflammatory demyelinating polyneuropathy and anti-MAG peripheral neuropathy.

In the present invention, the sensorineural hearing loss is preferably ototoxic hearing loss, but the present invention is not limited thereto. In addition, sensorineural hearing loss may be caused by damage to inner ear hair cells and surrounding tissues.

Ototoxic drugs are drugs or chemicals that damage the auditory function or balance function of the body, and mainly cause damage to the inner ear. These ototoxic drugs include antibiotics, anticancer drugs, diuretics (e.g., acetazolamide, furosemide, bumetanide, ethacrynic), and the like, and in particular, aminoglycoside antibiotics.

In the present invention, the ototoxic drugs may be preferably one or more selected from the group consisting of cisplatin, carboplatin, amikacin, arbekacin, kanamycin, gentamicin, neomycin, netilmicin, dibekacin, sisomicin, streptomycin, tobramycin, livodomycin, and paromomycin, but the present invention is not limited thereto.

The ototoxic drugs may be anticancer agents that cause ototoxicity, include cisplatin, carboplatin, oxaliplatin, bleomycin and vincristine, and more preferably include cisplatin, but the present invention is not limited thereto.

Cisplatin (cis-diaminedichloroplatinum (II), CDDP) of the present invention is an anti-tumor drug used to treat various tumors including breast cancer, bladder cancer, gastric cancer, cervical cancer, and head and neck cancer. Cisplatin is a heavy metal compound containing platinum, has a structure in which two chlorine atoms and two ammonia molecules are bonded to each other in a cis form around a platinum atom, and bonds to two adjacent guanines on the DNA strand to form intra-chain cross-links to thereby inhibit DNA synthesis. That is, cisplatin is known to be adhered to the DNA double-helix structure present in the nucleus of cancer cells to inhibit DNA replication, thereby inhibiting the growth and proliferation of cancer cells and exhibiting anticancer effects. However, cisplatin has limited clinical usefulness due to serious side effects such as ototoxic hearing loss. In fact, the majority of head and neck cancer patients treated with cisplatin are known to suffer from ototoxic hearing loss. This ototoxicity is initially evident as high-frequency hearing loss and then gradually causes hearing loss throughout the entire audible frequency range, as well as vestibular malfunction such as an abnormal balance. In order to prevent ototoxic hearing loss, research is underway on thiol-based drugs such as sodium thiosulfate, calcium channel blockers such as N-acetylcysteine, D- and L-methionine, flunarizine, and caspase inhibitors, but there is no currently available drug to date. As described above, cisplatin anticancer drugs are already known to have ototoxicity-related side effects, but they are still used due to the excellent anticancer effects thereof, and there are no other preventive or therapeutic drugs therefor. Therefore, there is an urgent need for an effective method and drug capable of preventing ototoxic hearing loss, which is a side effect of ototoxic drugs.

The known mechanisms of ototoxic hearing loss caused by cisplatin include an increase in reactive oxygen species (ROS) and subsequent lipid peroxidation and DNA damage, but various mechanisms have not been clearly identified yet.

The exchange of information between cells is caused when signals from external chemicals (e.g. hormones, growth factors, neurotransmitters, etc.) are recognized by specific receptors present in the cell membrane. As a result, various signals are transmitted into cells and second messengers are produced, mediated and amplified. Representative secondary messengers are cyclic nucleotides (e.g., cAMP and cGMP) and inositol 1,4,5-trisphosphate (IP3). The concentration of cyclic adenosine monophosphate (cAMP) in the cell is increased by the conversion of ATP to cAMP through adenylate cyclase, which activates protein kinase (PKA) and phosphorylates cAMP-response-element-binding protein (CREB). CREB binds to the cAMP response element (CRE) in DNA to promote various transcription factors to thereby regulate various cellular functions.

A gap junction is a membrane structure formed between two adjacent cells, and is a channel through which small hydrophilic substances of 1 kDa or less are passively diffused. In general, the inner ear gap junction is involved in the local circulation of $K^+$ ions and plays a major role in maintaining the high potential of extracellular lymph fluid, which is essential for auditory function. In addition, it has been observed that the cell survival pathway can be regulated by the regulation of the gap junction in a toxic environment. This is considered to be due to the delivery and signaling of intercellular ions and secondary messenger substances (cAMP, cGMP, IP3, DAG, etc.) by the gap junction. A similar study experimentally identified that cAMP substance intertransfer between bone cells is important for osteoblast differentiation, which is dependent on the gap junction formed by connexin 43 (Aditi Gupta et al., *Cell Signal.* 28(8):1048-57, 2016). In addition, it has been reported that renal toxicity caused by cisplatin anticancer drugs decreases cisplatin-induced oxidative damage in kidney cells when AMP activity is induced (Mishima K et al., *Free Radic. Biol. Med.* 40(9):1564-77, 2006). Retinoic acid increases the amount of connexin protein, which is a constituent protein of the gap junction, or promotes dephosphorylation of connexin to increase channel function.

Based on this mechanism, the present invention identifies a secondary messenger substance capable of preventing and treating cisplatin-induced ototoxic hearing loss and the effect of preventing or treating hearing loss by forskolin and retinoic acid as drugs capable of enhancing the effect thereof.

In the present invention, the composition may inhibit apoptosis of auditory cells. The apoptosis of auditory hair cells may be induced by an ototoxic drug.

As used herein, the term "hearing loss" or "hearing impairment" refers to impairment of the sense of recognizing sound and includes a defect in the ability to recognize sound caused thereby. The hearing impairment may be due to damage to the auditory hair cells or nerve cells, and includes damage to cells present in the organ of Corti or the cochlea. The hearing impairment may be caused by a genetic disorder, noise, ototoxicity, or any other specific stressor. Defects in the ability to recognize sound caused by hearing impairment include sensorineural hearing loss, conductive hearing loss, combined hearing loss, mild (25 to 40 dB), moderate (41 to 55 dB), moderately severe (56 to 70 dB), severe (71 to 90 dB), and very severe (greater than 90 dB) hearing loss, pre-language and post-language hearing loss, unilateral hearing loss (affecting one ear) and bilateral hearing loss (affecting both ears), or any combination thereof, i.e. sensorineural/severe/post-language/bilateral hearing loss.

As used herein, the term "cochlea" refers to a part of the inner ear that is associated with hearing. The cochlea is a spiral tubular structure wound like a snail. The interior of the cochlea is divided into three regions, which are distinguished by the location of the vestibular membrane and the basilar membrane. The part above the vestibular membrane is referred to as "scala vestibuli", which extends from the oval window to the apex of the cochlea, and contains perilymph, which is an aqueous liquid having low potassium content and high sodium content. The basilar membrane defines the "scala tympani", which extends from the apex of the cochlea to the round window, and also contains perilymph. The basilar membrane contains a number of rigid fibers, which gradually increase in length from the round window to the apex of the cochlea. The fibers of the basilar membrane are vibrated when activated by sound. The cochlear duct is positioned between the scala vestibuli and the scala tympani, and the distal end thereof is a closed sac at the apex of the cochlea. The cochlear duct contains endolymph, which is similar to cerebrospinal fluid and has a high potassium content.

The auditory organ known as the "organ of Corti" is located on the basilar membrane and extends upwards to the cochlear duct. The organ of Corti contains hair-like hair cells having protrusions extending from the free surface thereof, and contacts a gelatinous surface called the "tectorial membrane". The hair cells do not have axons, but are surrounded by sensory nerve fibers that form the cochlear branches of vestibulocochlear nerves (brain nerves VIII).

In the present invention, the composition may further comprise at least one additive selected from the group consisting of suitable carriers, excipients, disintegrants, sweeteners, coatings, swelling agents, antifrictions, slip modifiers, flavors, antioxidants, buffers, bacteriostats, diluents, dispersants, surfactants, binders and lubricants which are commonly used for the preparation of compositions.

The composition of the present invention may comprise a pharmaceutically acceptable carrier, and the term "pharmaceutically acceptable carrier" refers to a carrier or diluent that does not impair the biological activities or properties of the administered compound without irritating an organism.

Specifically, the carrier, excipient and diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration may include, but are not limited to, tablets, pills, powders, granules, capsules and the like, and these solid formulations may be prepared by mixing the composition with at least one excipient, for example, starch, calcium carbonate, sucrose, lactose, gelatin, or the like. In addition to simple excipients, lubricants such as magnesium stearate and talc are also used. Liquid formulations for oral administration may be suspensions, oral liquids and solutions, emulsions, syrups and the like, and may contain various excipients such as wetting agents, sweeteners, fragrances, preservatives and the like, in addition to water and liquid paraffin, which are simple diluents that are commonly used.

Formulations for parenteral administration include sterilized aqueous solutions, non-aqueous solutions, suspensions, emulsions, freeze-dried preparations, and suppositories. Propylene glycol, polyethylene glycol, vegetable oil such as olive oil, and injectable ester such as ethyl oleate may be used as the non-aqueous solvent and suspending agent. Formulations for parenteral administration may be prepared in an injectable form such as subcutaneous injection, intravenous or intramuscular injection, or in a spray form such as an aerosol that allows inhalation through suppository insertion or the respiratory tract. A formulation for injection may be prepared as a solution or suspension by mixing water with a stabilizer and optionally a buffer and placing the same into an ampoule or vial for single (unit) administration. Formulations for injection as a suppository may be prepared as a composition for rectal administration such as a suppository or enema containing a conventional suppository base such as cocoa butter or another glyceride. When formulated as a spray, such as an aerosol, a propellant or the like may be blended with an additive so that the water-dispersed concentrate or wet powder is dispersed.

In the present invention, the pharmaceutical composition may be provided as any one formulation selected from the group consisting of injections, granules, powders, tablets, pills, capsules, suppositories, gels, suspensions, emulsions, drops or solutions according to a conventional method.

In another aspect, the present invention is directed to an anticancer adjuvant comprising forskolin and retinoic acid as active ingredients for ameliorating sensorineural hearing loss.

In another aspect, the present invention is directed to a complex preparation for anticancer treatment comprising the anticancer adjuvant and an anticancer drug as active ingredients.

The pharmaceutical composition comprising forskolin and retinoic acid as active ingredients according to the present invention can prevent or ameliorate hearing loss caused by anticancer drugs, so cancer can be treated by stably administering an anticancer agent, without causing a side effect on hearing loss, even when long-term administration of the anticancer agent is inevitable.

In addition, the pharmaceutical composition comprising forskolin and retinoic acid as active ingredients according to the present invention may be provided as a pharmaceutical complex preparation for anticancer treatment that can alleviate the side effects of anticancer drugs.

The pharmaceutical complex preparation may comprise 0.01 to 90 parts by weight, 0.1 to 90 parts by weight, 1 to 90 parts by weight, or 10 to 90 parts by weight of forskolin and retinoic acid based on the total of 100 parts by weight, but is not limited thereto. The content of the pharmaceutical complex preparation may vary depending on the patient's condition and the type and progression of the disease.

In the present invention, the molar ratio of forskolin and retinoic acid in the complex preparation for anticancer treatment is preferably 1:0.5 to 1:10, more preferably 1:1 to 1:5, and most preferably 1:2 to 1:3, but is not limited thereto.

In another aspect, the present invention is directed to a method of preventing or treating sensorineural hearing loss comprising administering forskolin and retinoic acid.

In another aspect, the present invention is directed to a use of forskolin and retinoic acid for the prevention or treatment of sensorineural hearing loss.

In another aspect, the present invention is directed to a use of forskolin and retinoic acid for the preparation of a medicament for preventing or treating sensorineural hearing loss.

As used herein, the term "administration" refers to an action of introducing the composition according to the present invention into a subject by any appropriate method, and the route of administration of the composition may be any general route, so long as it enables the composition to be delivered to a target tissue.

The composition may be administered orally, intraperitoneally, intravenously, intramuscularly, subcutaneously, intradermally, endonasally, intrapulmonarily, rectally, intranasally, intraperitoneally, or intrathecally, but is not limited thereto. The composition according to the present invention may be simultaneously administered with the anticancer agent, or may be administered separately from the anticancer agent at a predetermined interval before or after the administration of the anticancer agent. The administration may be performed once a day, or may be divided into several doses, which does not limit the scope of the present invention. The preferred dosage of forskolin and retinoic acid may vary depending on the condition and weight of the patient, the type and severity of the disease, the form of the drug, and the route and duration of administration, and may be appropriately selected by those skilled in the art. According to an embodiment of the present invention, the daily dose may be 0.01 to 200 mg/kg, specifically 0.1 to 200 mg/kg, and more specifically 0.1 to 100 mg/kg, but is not limited thereto.

As used herein, in the term "prevention or treatment", "prevention" refers to any action that suppresses or delays the onset of hearing impairment or hearing loss by administration of the pharmaceutical composition comprising forskolin and retinoic acid as active ingredients according to the present invention, and "treatment" refers to any action that can ameliorate or beneficially alter hearing impairment or hearing loss through administration of the pharmaceutical composition.

In another aspect, the present invention is directed to a method of ameliorating sensorineural hearing loss comprising administering the anticancer adjuvant comprising forskolin and retinoic acid as active ingredients.

In another aspect, the present invention is directed to a method of ameliorating sensorineural hearing loss comprising administering the complex preparation for anticancer treatment comprising forskolin and retinoic acid as active ingredients.

In another aspect, the present invention is directed to a use of the anticancer adjuvant comprising forskolin and retinoic acid as active ingredients for the amelioration of sensorineural hearing loss.

In another aspect, the present invention is directed to a use of the complex preparation for anticancer treatment comprising forskolin and retinoic acid as active ingredients for the amelioration of sensorineural hearing loss.

EXAMPLE

Hereinafter, the present invention will be described in more detail with reference to examples. However, it will be obvious to those skilled in the art that these examples are provided only for illustration of the present invention and should not be construed as limiting the scope of the present invention based on the subject matter of the present invention.

Example 1: In-Vivo Experiment Using Tumor-Induced Ototoxic Hearing Loss Animal Model In order to exclude mice having congenitally abnormal hearing, a preliminary hearing test was performed on all mice before the experiment. An auditory brainstem response (ABR) test was conducted on the immunodeficient Balb/c/nu/nu mice and then a lung cancer cell line (A549) was xenografted subcutaneously into the mice to produce a tumor-induced animal model (FIG. 1).

The produced tumor-induced animal model was classified into (1) a physiological saline group (Vehicle), (2) a forskolin administration group (forskolin), (3) a cisplatin administration group (cisplatin), and (4) a cisplatin+forskolin combination administration group (cisplatin+forskolin), and each drug was administered to each group. Cisplatin was administered at 12 mg/kg 5 times a week, forskolin was administered at 2.5 mg/kg 6 times a week for a total of 2 weeks, the auditory brainstem response test was performed again 1 week after all administration was completed, and hematoxylin-eosin staining was performed for histological analysis. The auditory brainstem response (ABR) test is a method that determines the minimum stimulus level (dB) as a hearing threshold when applying tone burst sounds at 16 kHz and 32 kHz using a TDT ABR device.

Figure 3A:
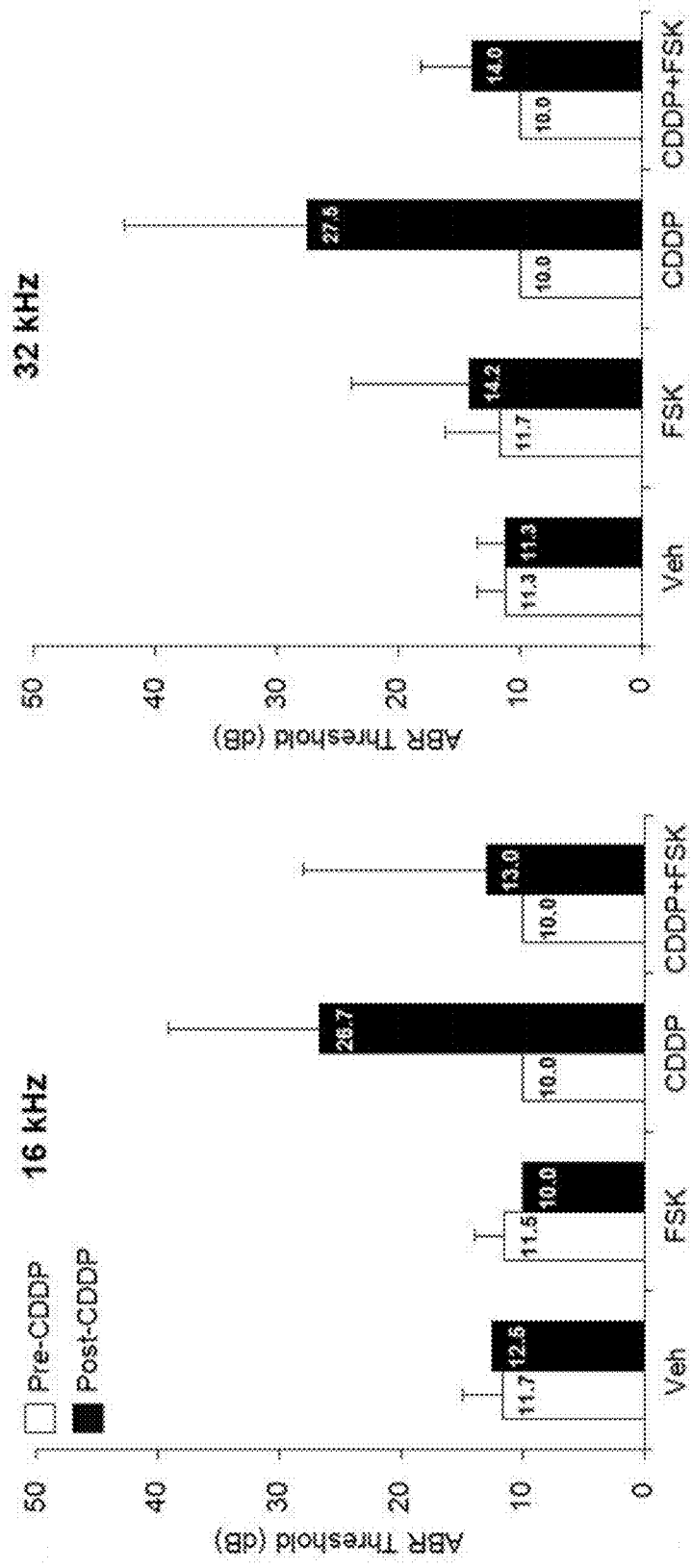
FIG. 3A shows ABR measured at 16 and 32 kHz before and after treating a tumor-induced model with cisplatin.

The result of the auditory brainstem response (ABR) test showed that the hearing threshold increased to 29 dB at 16 kHz and 31 dB at 32 kHz in the cisplatin-treated group. The cisplatin+forskolin combination administration group was found to have an effect of preventing hearing loss based on the hearing threshold decreased to 13.3 dB at 16 kHz and 16.7 dB at 32 kHz (FIG. 3A).

Figure 3B:
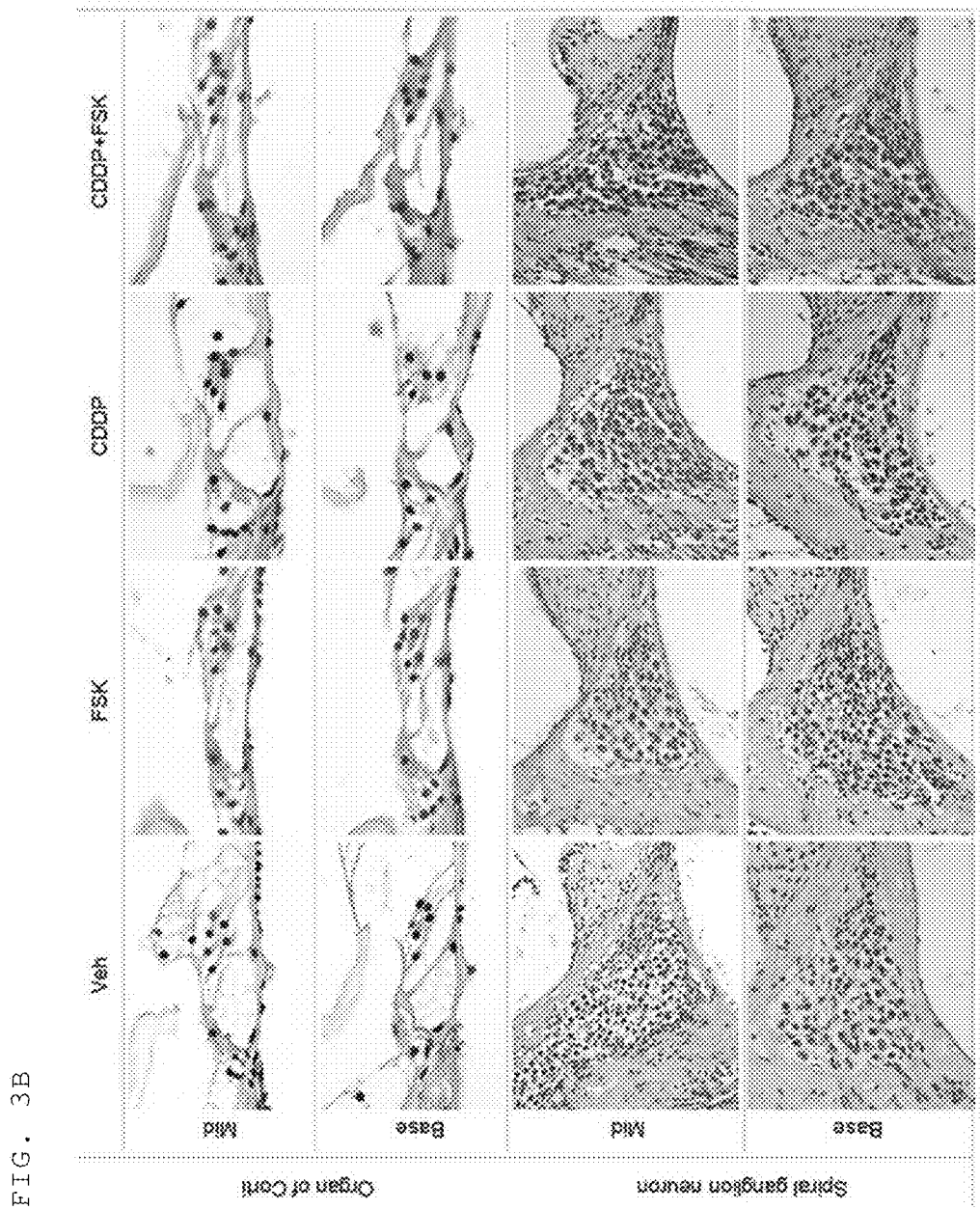
FIG. 3B shows the result of H&E staining in basal turn and middle turn sites of the cochlea.

In addition, loss and damage of the auditory hair cells, supporting cells and spiral ganglion cells in the organ of Corti during the basal and middle turns of the cochlea were evaluated using hematoxylin-eosin staining. As a result, a number of the auditory outer hair cells during the basal and middle turns were found to be lost by the administration of cisplatin, but most auditory outer hair cells were preserved by the administration of forskolin (FIG. 3B).

Example 2: Cisplatin Anticancer Effect in Tumor-Induced Ototoxic Hearing Loss Animal Model After tumor formation in the tumor-induced ototoxic hearing loss animal model of Example 1, mice were randomly classified, and then (1) physiological saline (vehicle), (2) forskolin, (3) cisplatin or (4) a combination of cisplatin and forskolin was administered intraperitoneally to the mice for 5 days, and then the mice were reared for 7 days.

Figure 4A:
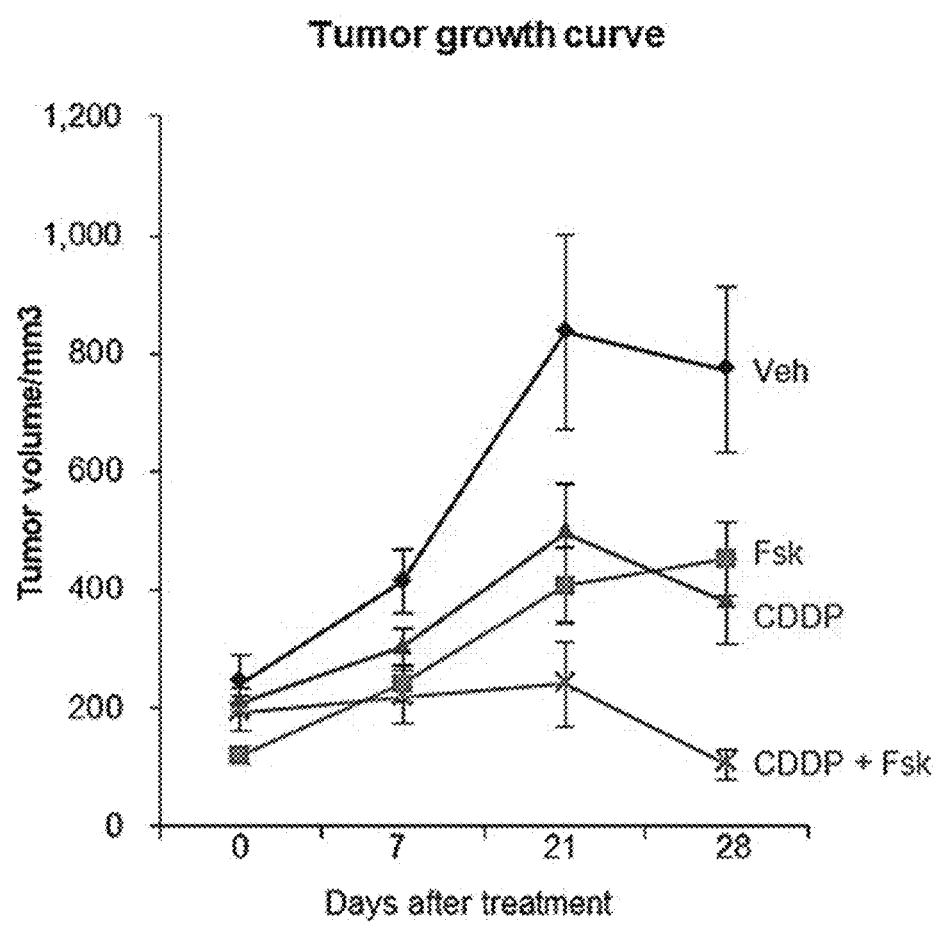
FIG. 4A shows tumor volume change.
Figure 4B:
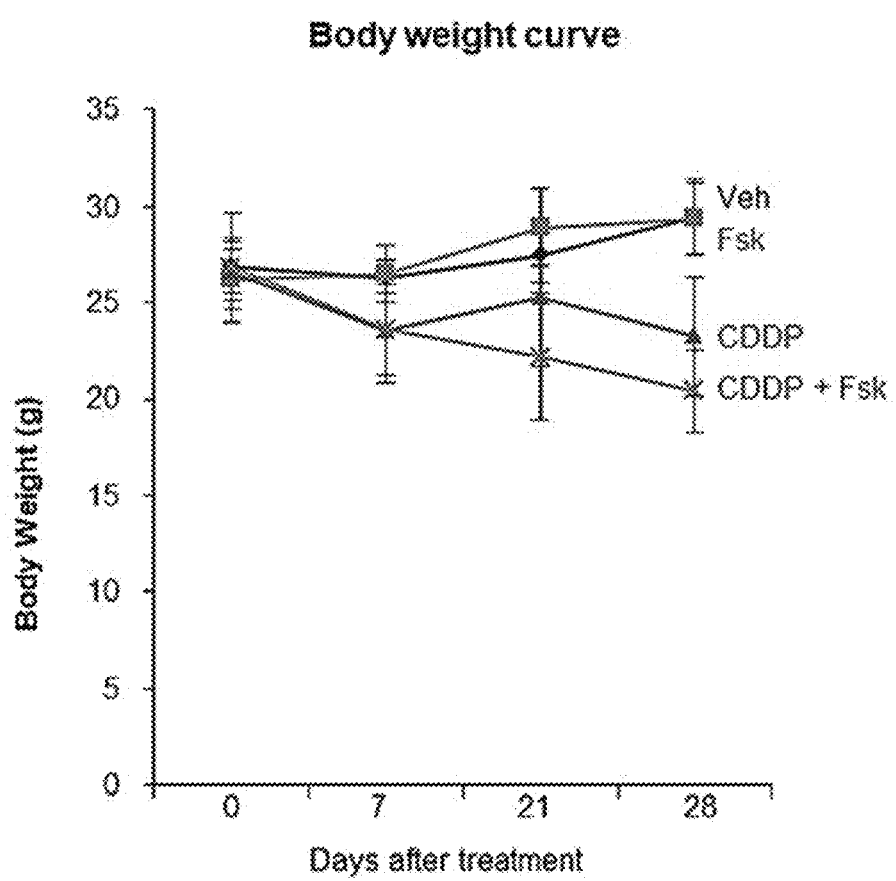
FIG. 4B shows weight change.
Figure 4C:
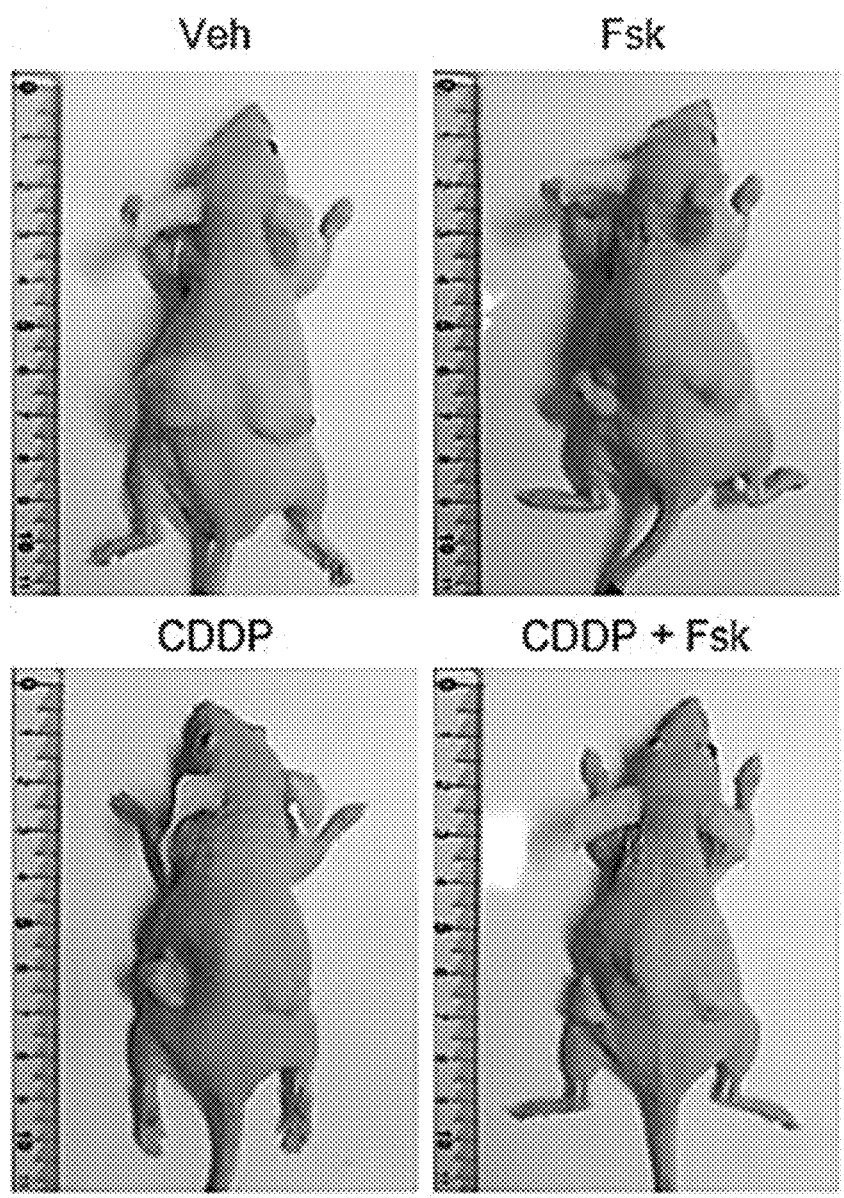
FIG. 4C shows mouse appearance.
Figure 4D:
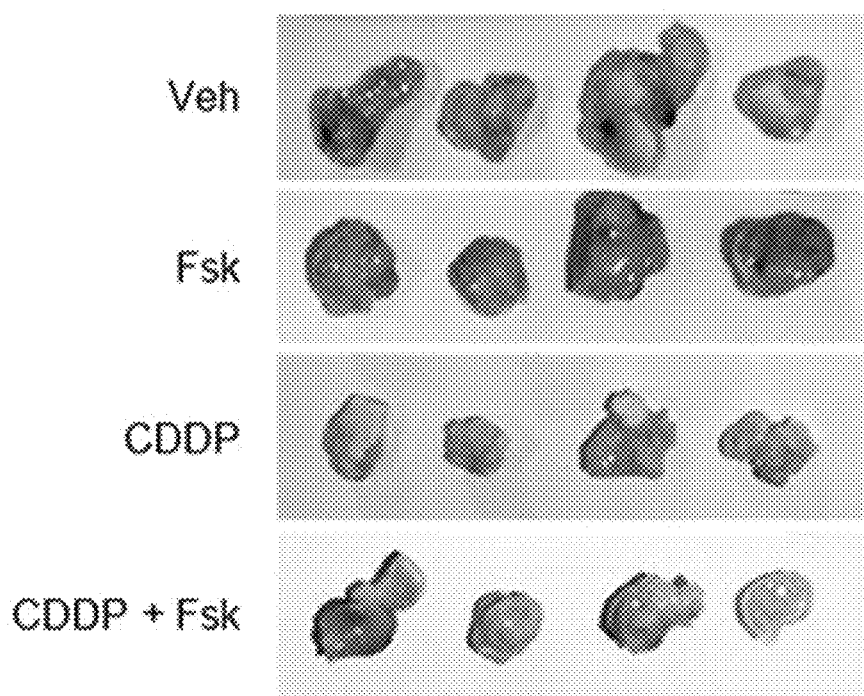
FIG. 4D shows separated tumor.
Figure 4E:
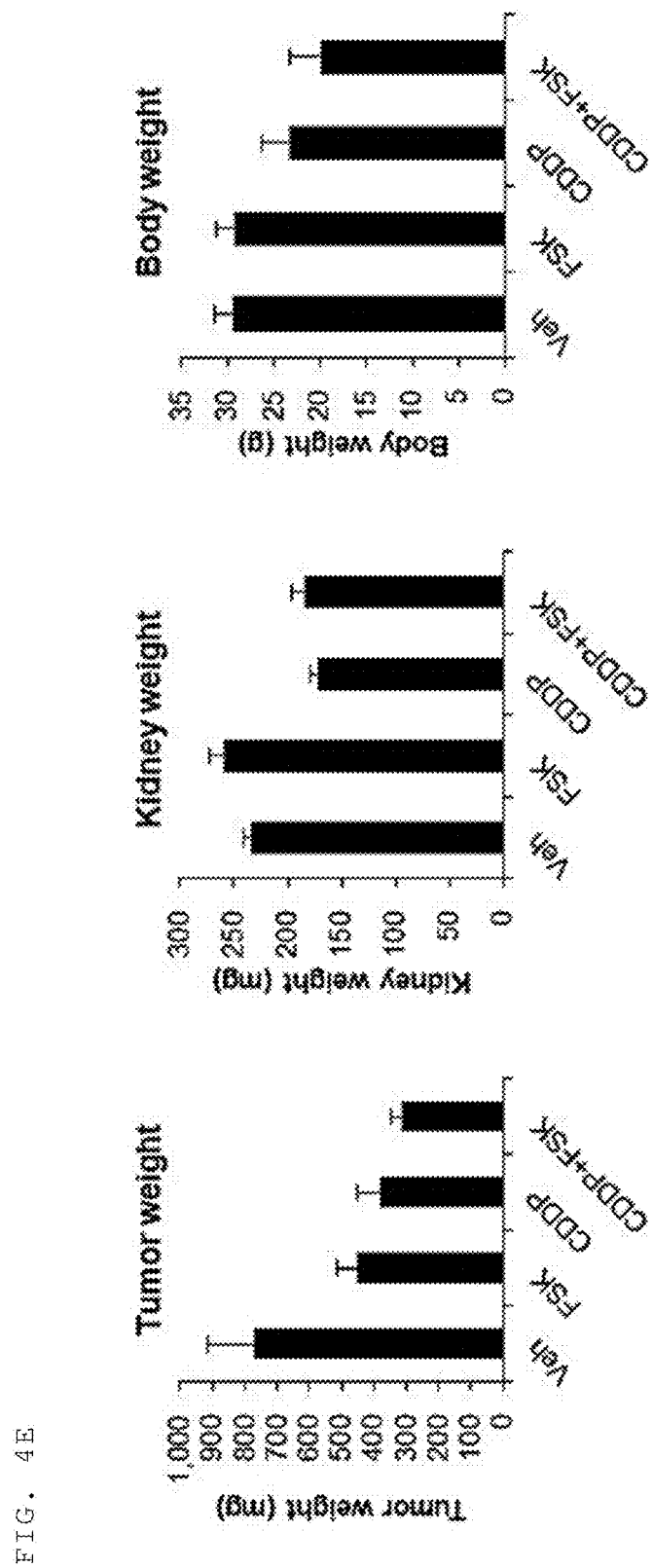
FIG. 4E shows tumor weight, kidney weight, and body weight after administration of each of physiological saline (vehicle), forskolin, cisplatin, and a combination of cisplatin and forskolin to a tumor-induced model.

The average tumor volume and body weight of each group were measured every week (FIGS. 4A and 4B). In addition, the weight of each of the extracted tumor and kidney was also measured (FIG. 4E).

As a result, the group administered with cisplatin alone as well as the group administered with the combination of cisplatin and forskolin exhibited an effect of reducing a tumor size by about 50% compared to the control group, and no statistical significance was observed between the two groups. That is, it could be seen that the anticancer effect of cisplatin in the tumor-induced animal model was not affected by forskolin. It was found that forskolin has an effect of avoiding hearing loss by preventing damage to auditory cells, while having no effect on the anticancer effect of cisplatin.

Figure 2:
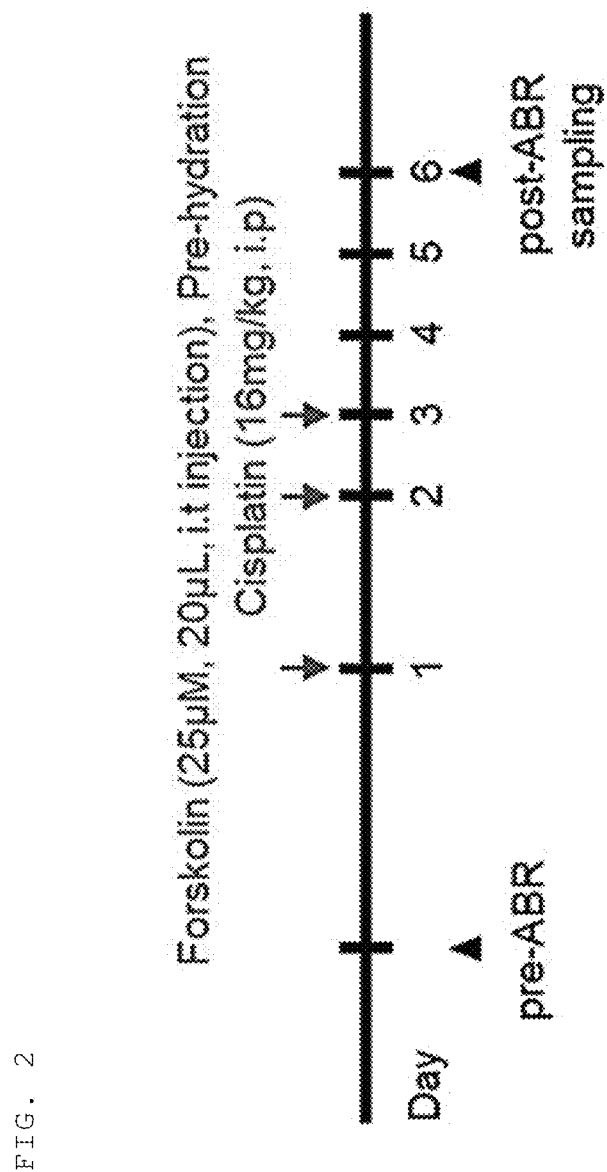
FIG. 2 is a schematic diagram showing an in-vivo experiment using an SD-rat general animal model.

Example 3: In-Vivo Experiment Using Conventional Ototoxic Hearing Loss Animal Model In order to exclude mice having congenitally abnormal hearing, a preliminary hearing test was performed on all mice before the experiment. An auditory brainstem response (ABR) test was conducted on 7-week-old SD (Sprague-Dawley) rats and then 16 mg/kg/7 ml of a cisplatin anticancer drug was administered intraperitoneally once to induce ototoxic hearing loss (FIG. 2).

Before and after cisplatin administration, forskolin was intratympanically injected (IT) into one ear once in an amount of 25 µM in 20 µL a total of two times, and physiological saline containing DMSO as a control group was injected into the other ear. After 5 days, an auditory brainstem response (ABR) test and a histological examination were performed to evaluate the effect of preventing induction of forskolin-cAMP activity against ototoxic hearing loss.

Figure 5A:
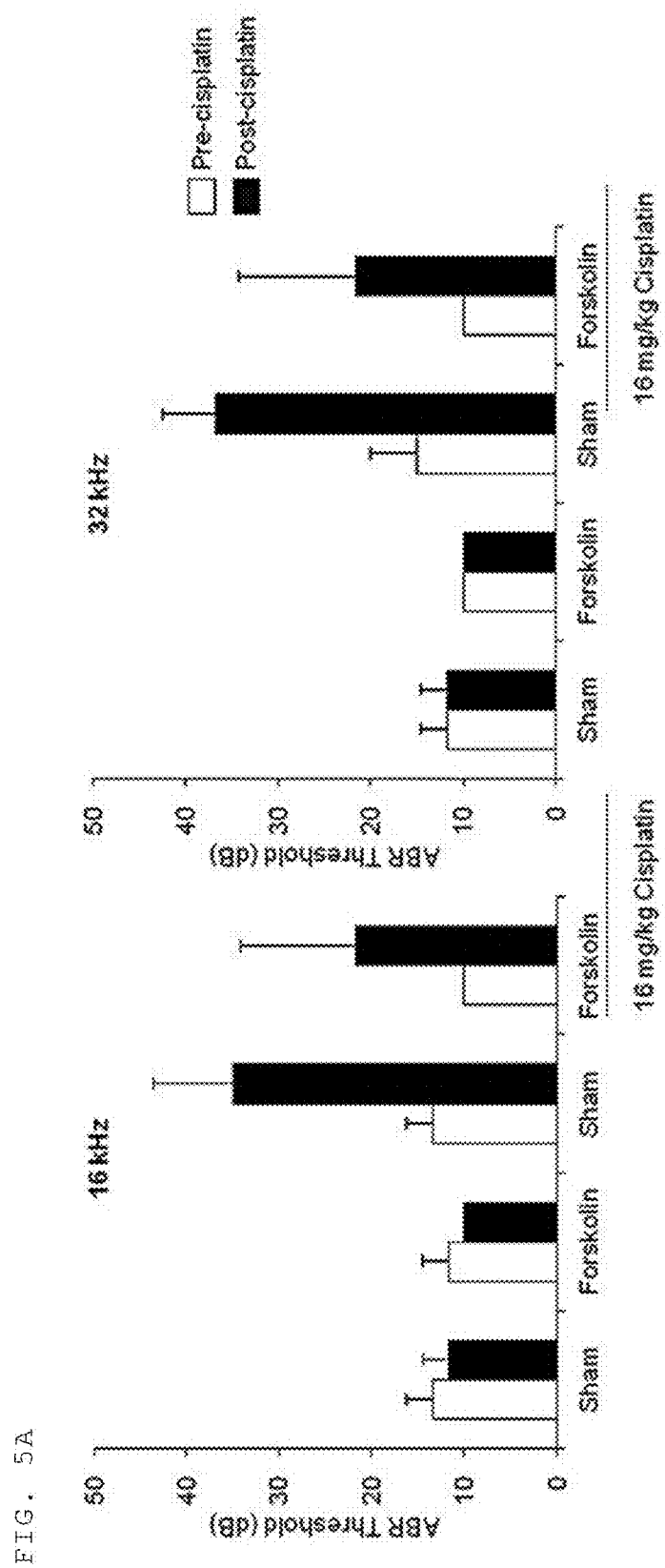
FIG. 5A shows ABR measured at 16 and 32 kHz before and after administration of cisplatin to the SD-rat general animal model, wherein forskolin is injected into the right ear and DMSO is injected into the left ear.
Figure 5B:
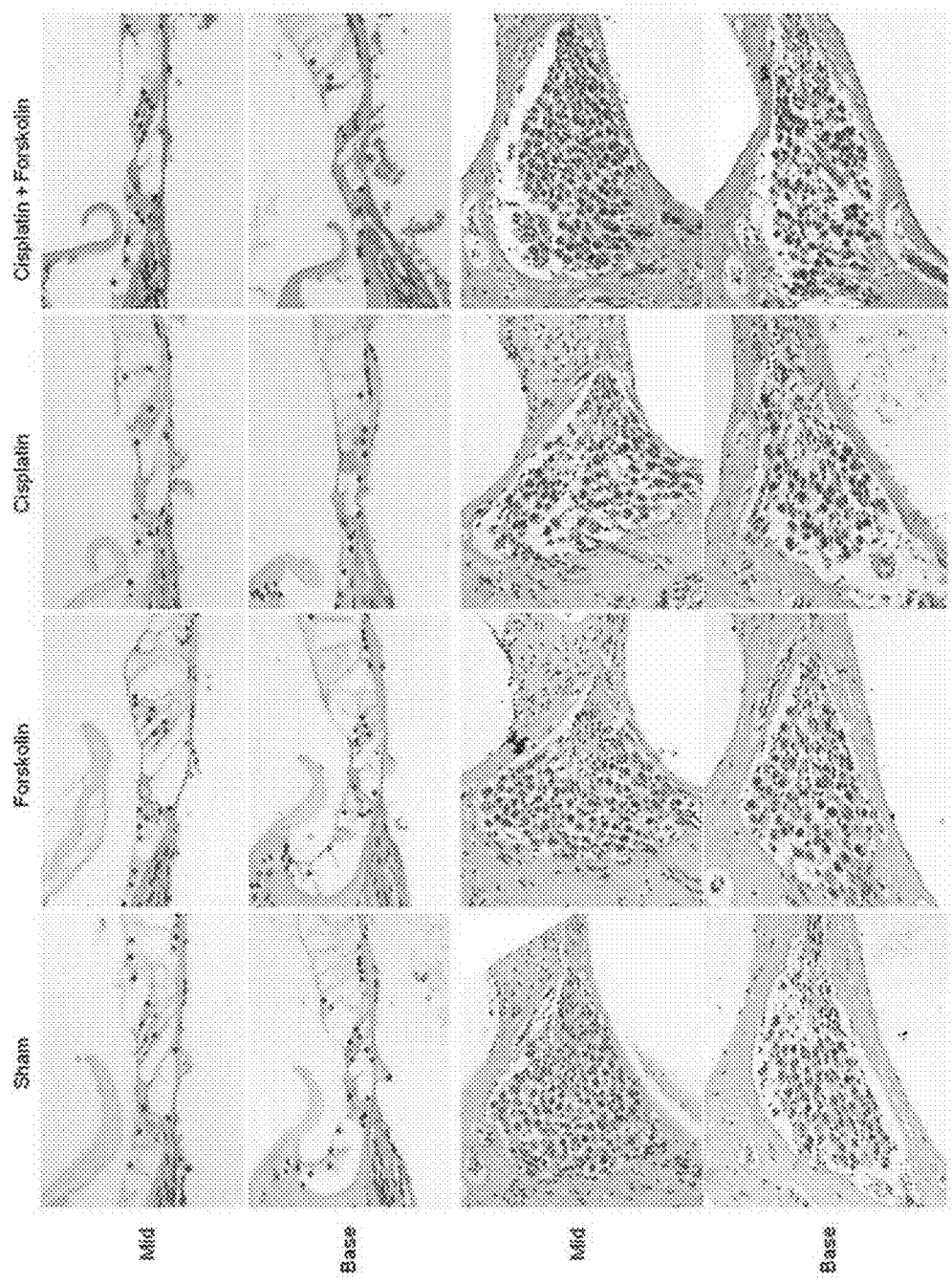
FIG. 5B shows the result of H&E staining in middle turn and basal turn sites.

As a result, a decrease in hearing threshold in the ear injected with forskolin in the group to which cisplatin was administered intraperitoneally was observed (FIG. 5A). In addition, loss of a number of auditory hair cells during the basal and middle turns in the cochlea was observed in the ears administered with cisplatin in the control group, but auditory hair cells were observed to be preserved in the ears administered with the combination of cisplatin and forskolin (FIG. 5B).

Example 4: Inhibition of Apoptosis by Forskolin and Retinoic Acid in Auditory Cell Line An auditory cell line expressing auditory genes (HEI-OC1; House-Ear Institute-organ of Corti 1) was used, and the HEI-OC1 cells were incubated in DMEM medium (Dulbecco's modified Eagle's Medium) containing a high concentration of glutamine, supplemented with 10% fetal bovine serum (FBS) and 25 U/ml of interferon gamma at 33° C. and 10% $CO_2$. The cells were treated with cisplatin at a concentration of 25 μM, and the effects of forskolin and retinoic acid were analyzed under conditions in which about 40 to 50% of cells were killed by cisplatin ototoxicity.

In order to analyze the effects of forskolin and retinoic acid on ototoxicity, experimental groups were classified into (1) normal, (2) forskolin, (3) retinoic acid, (4) cisplatin, (5) cisplatin+forskolin, (6) cisplatin+retinoic acid, (7) cisplatin+forskolin+retinoic acid. Cisplatin was administered in an amount of 25 μM, forskolin was administered in an amount of 20 μM, and retinoic acid was administered in an amount of 50 μM. Then, viable cells were observed using calcein AM, a fluorescent stain applicable to live cells, and cleaved PARP and caspase 3, as apoptosis markers, were identified at the protein level.

Figure 6A:
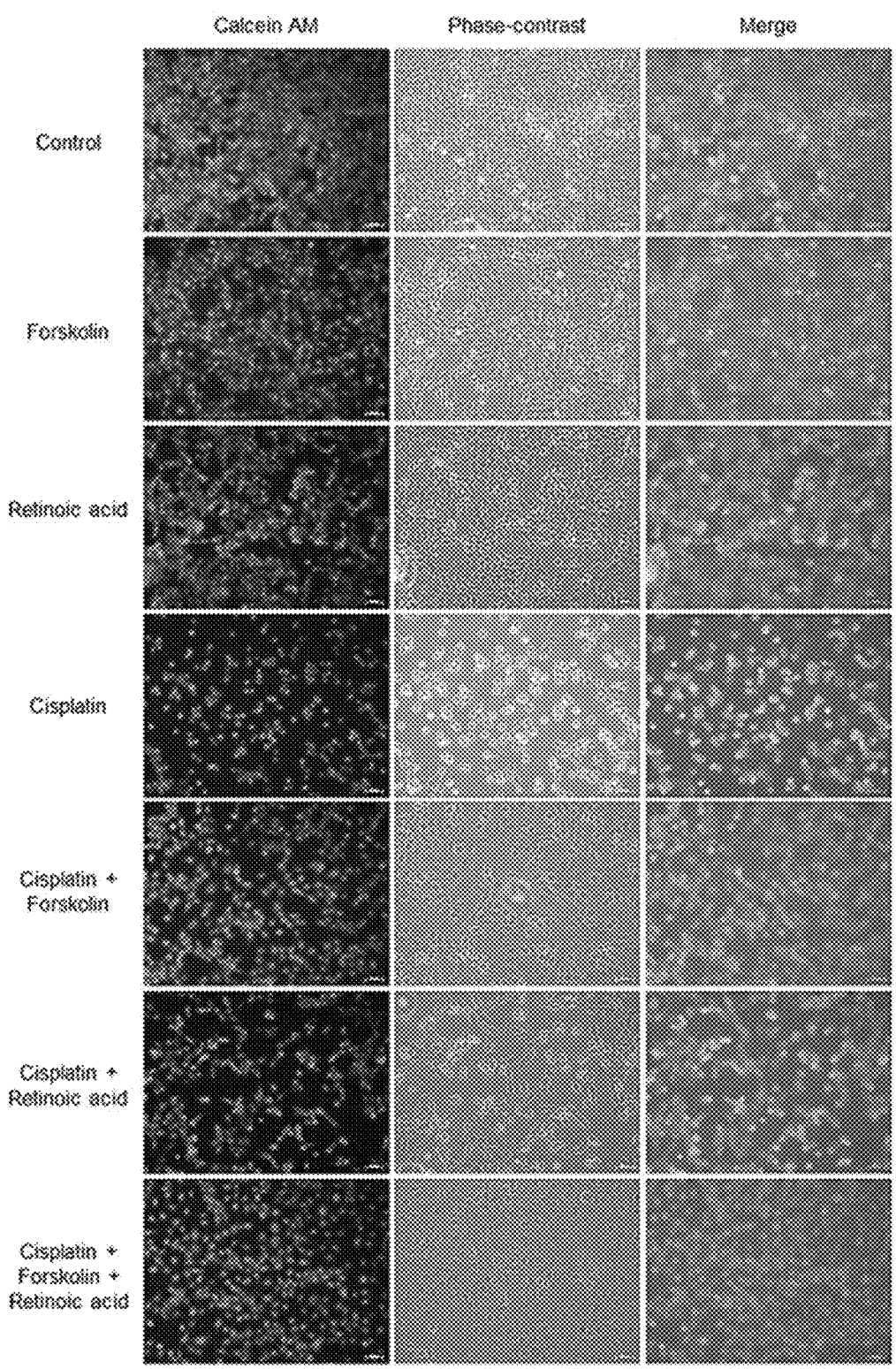
FIG. 6A shows the result of analysis of calcein AM-labeled fluorescence and phase difference images for determining the synergistic effect of forskolin with retinoic acid in a REI-OC1 auditory cell line.
Figure 6B:
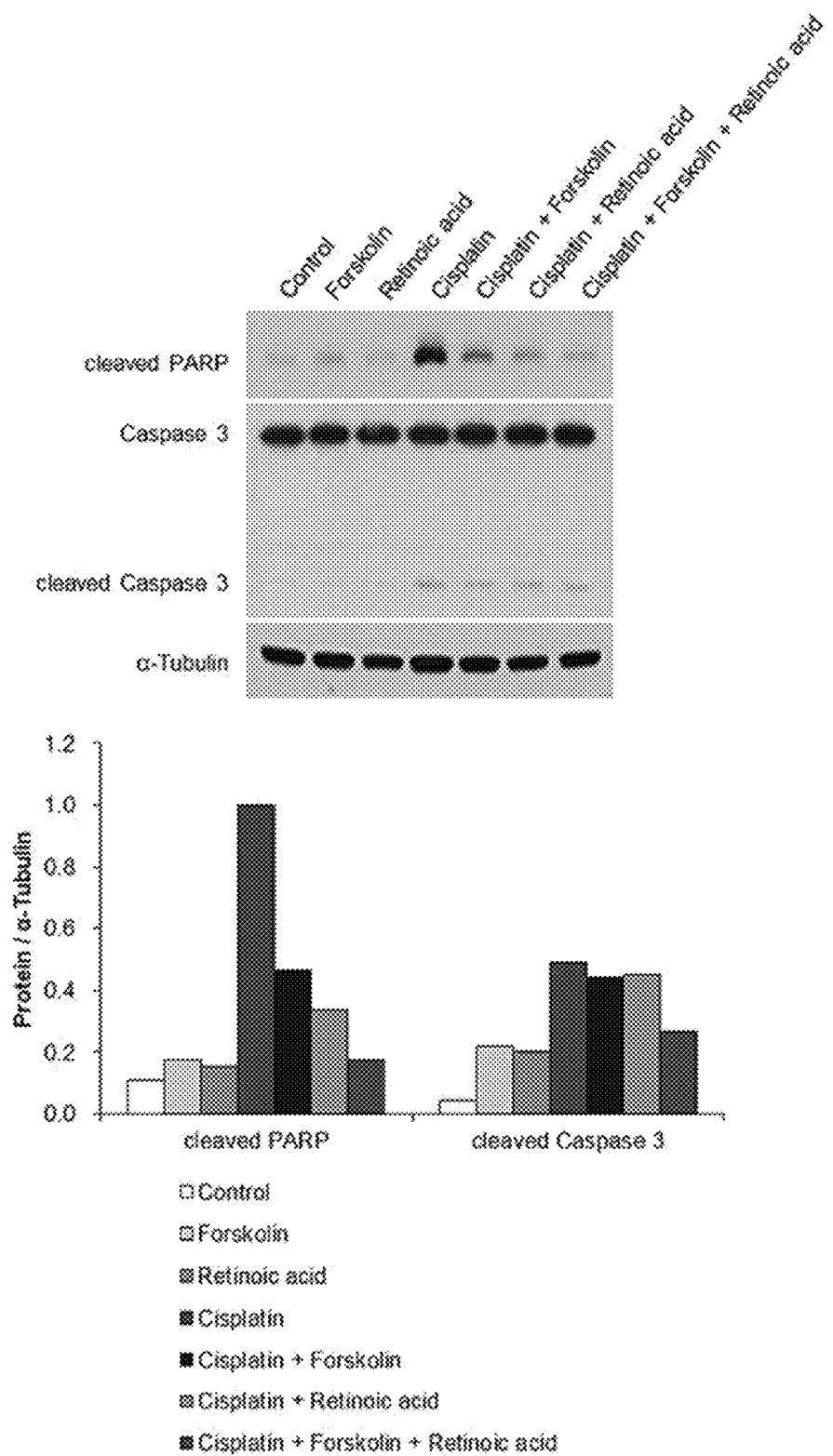
FIG. 6B shows the result of western blot analysis for determining cleaved PARP and caspase-3 expression.

As a result, apoptosis of cisplatin-induced auditory cell lines was observed through calcein staining and expression of cleaved PARP and caspase 3 proteins, which are markers related to apoptosis, and treatment with forskolin or retinoic acid alone was found to exhibit an effect of increasing cell viability (FIGS. 6A-6B). In addition, it was found that treatment with a combination of forskolin and retinoic acid exhibited a synergistic effect compared to single treatment with forskolin or retinoic acid alone.

Therefore, when cisplatin administration is inevitable, forskolin and retinoic acid can be useful for preventing hearing loss in patients.

INDUSTRIAL APPLICABILITY

The pharmaceutical composition for preventing or treating sensorineural hearing loss comprising forskolin and retinoic acid as active ingredients according to the present invention is highly effective in preventing, ameliorating or treating hearing loss caused by ototoxic drugs during anticancer therapy, thus being useful as a pharmaceutical complex preparation capable of alleviating side effects of anticancer agents as well as a therapeutic or prophylactic agent for sensorineural hearing loss.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A method of treating sensorineural hearing loss in a subject in need thereof comprising administering a composition comprising forskolin and retinoic acid as active ingredients.

2. The method according to claim 1, wherein the sensorineural hearing loss is ototoxic hearing loss caused by an ototoxic drug.

3. The method according to claim 2, wherein the ototoxic drug comprises one or more selected from the group consisting of cisplatin, carboplatin, amikacin, arbekacin, kanamycin, gentamicin, neomycin, netilmicin, dibekacin, sisomicin, streptomycin, tobramycin, livodomycin, and paromomycin.

4. The method according to claim 1, wherein the composition inhibits apoptosis of auditory cells.

5. The method according to claim 1, wherein the composition further comprises a pharmaceutically acceptable additive.

6. The method according to claim 5, wherein the pharmaceutically acceptable additive comprises one or more selected from the group consisting of an excipient, a binder, a slip modifier, a lubricant, a disintegrating agent, and a flavor.

7. The method of claim 1, wherein the composition is a pharmaceutical composition and further comprises a pharmaceutically acceptable carrier.

8. An anticancer adjuvant comprising forskolin and retinoic acid as active ingredients for ameliorating sensorineural hearing loss.

9. The anticancer adjuvant according to claim 8, wherein the sensorineural hearing loss is ototoxic hearing loss caused by an ototoxic drug.

10. The anticancer adjuvant according to claim 9, wherein the ototoxic drug comprises one or more selected from the group consisting of cisplatin, carboplatin, amikacin, arbekacin, kanamycin, gentamicin, neomycin, netilmicin, dibekacin, sisomicin, streptomycin, tobramycin, livodomycin, and paromomycin.

11. A method of anticancer treatment comprising administering a complex preparation comprising the anticancer adjuvant according to claim 8 and an anticancer drug as active ingredients.

* * * * *